US010910187B2

(12) United States Patent
Marconnet et al.

(10) Patent No.: US 10,910,187 B2
(45) Date of Patent: Feb. 2, 2021

(54) X-RAY TUBE CATHODE FLAT EMITTER SUPPORT MOUNTING STRUCTURE AND METHOD

(71) Applicant: General Electric Company, Schenectady, NY (US)

(72) Inventors: Andrew Marconnet, Milwaukee, WI (US); Gregory Steinlage, Milwaukee, WI (US); Sandhya Abhivandana Dammu, Milwaukee, WI (US); Evan Lampe, Milwaukee, WI (US); Donald Allen, Waukesha, WI (US); Michael Utschig, Milwaukee, WI (US); William Scott, Milwaukee, WI (US); David Bateman, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 21 days.

(21) Appl. No.: 16/140,980

(22) Filed: Sep. 25, 2018

(65) Prior Publication Data

US 2020/0098535 A1    Mar. 26, 2020

(51) Int. Cl.
*H01J 35/06*    (2006.01)
*H01J 9/18*    (2006.01)
*A61B 6/03*    (2006.01)
*G01V 5/00*    (2006.01)
*H01J 35/10*    (2006.01)

(52) U.S. Cl.
CPC .............. *H01J 35/06* (2013.01); *H01J 9/18* (2013.01); *A61B 6/032* (2013.01); *G01V 5/005* (2013.01); *H01J 35/10* (2013.01)

(58) Field of Classification Search
CPC .................................................. H01J 2235/068
See application file for complete search history.

(56) References Cited

U.S. PATENT DOCUMENTS

| | | | |
|---|---|---|---|
| 8,831,173 B2 | 9/2014 | Lemaitre | |
| 9,466,455 B2 | 10/2016 | Hubbard | |
| 2009/0060141 A1* | 3/2009 | Fritzler | H01J 35/065 378/134 |
| 2010/0284519 A1* | 11/2010 | Moore | H01J 1/20 378/136 |
| 2017/0092456 A1* | 3/2017 | Zhang | H01J 9/042 |
| 2018/0211810 A1* | 7/2018 | Sullivan | H01J 35/14 |

* cited by examiner

*Primary Examiner* — Hoon K Song (57) ABSTRACT

At least one emitter formed of an electron emissive material is positioned on a cathode assembly and is readily and reliably connected to at least one mounting member of the cathode assembly. The connections between the at least one emitter and an emitter support structure are formed directly between the at least one emitter and the emitter support structure by utilizing the at one mounting member on the emitter support structure that are positioned adjacent the at least one emitter and heated to secure the at least one emitter to the emitter support structure by welding the at least one mounting member to the at least one emitter and emitter support structure.

18 Claims, 4 Drawing Sheets

X-RAY TUBE CATHODE FLAT EMITTER SUPPORT MOUNTING STRUCTURE AND METHOD

BACKGROUND OF THE DISCLOSURE

The invention relates generally to X-ray tubes, and more particularly to structures for emitters utilized in an X-ray tube to properly position the emitters within the X-ray tube.

X-ray imaging systems may include an X-ray tube, a detector, and support structure for the X-ray tube and the detector. In operation, an imaging table, on which an object is positioned, may be located between the X-ray tube and the detector. The X-ray tube typically emits radiation, such as X-rays, toward the object. The radiation passes through the object on the imaging table and impinges on the detector. As radiation passes through the object, internal structures of the object cause spatial variances in the radiation received at the detector. The detector then emits data received, and the system translates the radiation variances into an image, which may be used to evaluate the internal structure of the object. The object may include, but is not limited to, a patient in a medical imaging procedure and an inanimate object as in, for instance, a package or other object in an X-ray scanner or computed tomography (CT) scanner.

Presently available X-ray tubes typically include a cathode assembly having one or more emitters thereon. The cathode assembly is oriented to face an X-ray tube anode, or target, which is typically a planar metal or composite structure. The space within the X-ray tube between the cathode and anode is enclosed within a vacuum housing.

The emitters functions as an electron source that releases electrons at high acceleration. Some of the released electrons may impact the target anode. The collision of the electrons with the target anode produces X-rays, which may be used in a variety of medical devices such as computed tomography (CT) imaging systems, X-ray imaging systems, and so forth. In thermionic cathode systems, an emitter is included that may be induced to release electrons through a thermionic effect, i.e., in response to being heated. This emitter is often a flat surface emitter (or a 'flat emitter') that is positioned on the cathode with the flat surface positioned orthogonal to the anode, such as that disclosed in U.S. Pat. No. 8,831,178, incorporated herein by reference in its entirety for all purposes. In the '178 patent a flat emitter with a rectangular emission area is formed with a very thin material having electrodes attached thereto, which can be significantly less costly to manufacture compared to emitters formed of wound (cylindrical or non-cylindrical) filaments and may have a relaxed placement tolerance when compared to a wound filament emitter.

Typical flat emitters are formed with an electron emissive material, such as tungsten, having a flat electron emission surface that generates electrons when heated above a certain temperature. Current is directly applied from the cathode through the flat emitter to generate heat in the emitter and results in the emitter surface reaching temperatures high enough to produce electron emission, typically above 2000 degrees Celsius (° C.).

In many X-ray tubes, at least one flat emitter is used to generate the electron beams utilized to create the X-rays emitted from the tube. In some X-ray tubes employing multiple, i.e., more than one emitter, the multiple emitters are oriented flat or planar with respect to one another within the cathode assembly and are electrically connected to one another to provide a current flow through the multiple emitters to enable concurrent operation of the emitters. The required electrical connection can readily be made during the construction of the emitters as the emitters are disposed in a planar configuration and can be formed with a planar electrical connection directly between the emitters. In this configuration, while the use of multiple emitters provides an increase in the beam strength and/or size, it is necessary to consequently increase the focusing capacity of the tube in order to properly direct the electron beam produced by the multiple planar flat emitters.

In other X-ray tubes employing a pair of flat emitters, the emitters are positioned at angles with respect to one another within the cathode assembly. The angled position of the emitters enable the electron beams created by the emitters to be focused more easily towards the desired focal spot based upon the direction of the electron beam emitted from the angled emitters. In certain prior art X-ray tubes, the angled pair of emitters are operated independently of one another in order to emit an electron beam that can be readily focused on the desired focal spot by the focusing components of the X-ray tube. In this configuration, the emitters do not need to be electrically connected to one another due to their independent operation.

However, in other X-ray tubes the pair of angled emitters are operated in conjunction with one another and thus need to be disposed in electrical connection with one another for current to flow between the emitters. However, the angled configuration of the emitters prevents any electrical connection from being created between the emitters during the formation of the emitters, similarly to a pair of planar emitters, as any bending or other deformation of the material forming the emitters after formation can significantly thin and/or weaken the material, greatly shortening the useful life of the emitter. As such, in the X-ray tubes employing angled pairs of emitters, the electrical connection of the emitters in prior art cathode assemblies is facilitated by the underlying structure of the cathode on which the emitters are secured. As such, the tolerance for the proper placement of the emitters on the cathode support structure is very small in order to ensure that the emitters are in electrical connection with the support structure and optionally one another. This in turn requires extremely precise manufacturing and placement of the emitters on the cathode to properly connect the emitters to the cathode and to one another.

In prior art cathode assemblies, the emitters are formed with apertures adjacent each end of the emitter. When positioned on the support structure, an amount of a filler material, such as metal, e.g., platinum, is positioned within the aperture. The filler material is subsequently heated in order to enable the filler material to flow over the emitter and into the aperture between the emitter and support structure to form a weld between the support structure and the emitter to hold the emitter in position on the support structure.

While the weld formed of the filler material is sufficient to hold the emitter on the support structure, the use of the filler material to weld the emitter to the support structure has certain deficiencies. As the emitter is only placed on the support structure prior to forming the weld, during the formation of the weld the position of the emitter may shift with respect to the support structure, causing the emitter to become misaligned with the electrical connections on the support structure. Further, as the filler material must flow through the aperture to contact the support structure, and the emitters can be angularly positioned on the support structure the heated filler material can flow unevenly through the aperture, causing the resulting weld to inaccurately hold the emitter to the support structure. Additionally, the placement of the filler material on the emitter and within the aperture is often difficult due to the small size of the aperture, e.g., less than 0.5 mm, and the angle of the emitter on the support structure. Thus, the filler material can be misaligned with the aperture, such that when heated, the filler material does not correctly and/or evenly flow over the emitter and/or into the aperture resulting in a sub-optimal weld being formed between the support structure and the emitter.

As a result, it is desirable to develop an emitter support structure system and method for the mounting of flat emitters that are angularly positioned with regard to one another within an X-ray tube that is designed to readily and reliably enable the proper connection of the emitters the support structure of the cathode assembly.

BRIEF DESCRIPTION OF THE DISCLOSURE

In the disclosure, At least one emitter formed of an electron emissive material is positioned on a cathode assembly and is readily and reliably connected to at least one mounting member of the cathode assembly. The connections between the at least one emitter and the emitter support structure are formed directly between the at least one emitter and the emitter support structure by utilizing the at least one mounting member on the emitter support structure that are positioned adjacent the at least one emitter and heated to form welds securing the at least one emitter to the emitter support structure.

According to one aspect of an exemplary embodiment of the invention, the at least one mounting member is formed integrally with the emitter support structure in order to properly locate the at least one mounting member on the emitter support structure. Further, the at least one emitter can be readily positioned on the emitter support structure in the proper position through the engagement of the at least one mounting member with corresponding at least one locating features on the at least one emitters. Once properly positioned on the emitter support structure by engagement with the at least one mounting member, the at least one emitter can be affixed to the emitter support structure by heating the at least one mounting member to form a weld between the at least one emitter and the emitter support structure.

The emitter support structure formed with the at least one mounting member thereon improves the speed and ease of manufacturing the cathode assembly by eliminating the need for a filler material while decreasing the time required for manufacturing the X-ray tube and the amount of variation in the cathode assembly manufactured utilizing the emitter support structure with the at least one mounting member thereon.

In another exemplary embodiment of the disclosure, an emitter support structure adapted for use with an X-ray tube includes an emitter attachment surface and at least one mounting member disposed on the emitter attachment surface.

In still another exemplary embodiment of the disclosure, an X-ray tube includes a cathode assembly and an anode assembly spaced apart from the cathode assembly, wherein the cathode assembly includes an emitter support structure including at least one mounting member thereon and at least one emitter disposed on the emitter support structure, the at least one emitter including at least one locating feature disposed around the at least one mounting member.

In another exemplary embodiment of a method of the disclosure, a method for forming a cathode assembly used in an X-ray tube includes the steps of providing an emitter support structure including an emitter attachment surface having at least one mounting member thereon, providing at least one emitter including at least one locating feature thereon, positioning the at least one emitter on the emitter support structure with the at least one locating feature disposed at least partially around the at least one mounting member and heating the at least one mounting member to secure the at least one emitter to the emitter attachment surface.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION OF THE DISCLOSURE

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Exemplary embodiments of the invention relate to an X-ray tube including an increased emitter area to accommodate larger emission currents in conjunction with microsecond X-ray intensity switching in the X-ray tube. An exemplary X-ray tube and a computed tomography (CT) imaging system employing the exemplary X-ray tube are presented.

Figure 1:
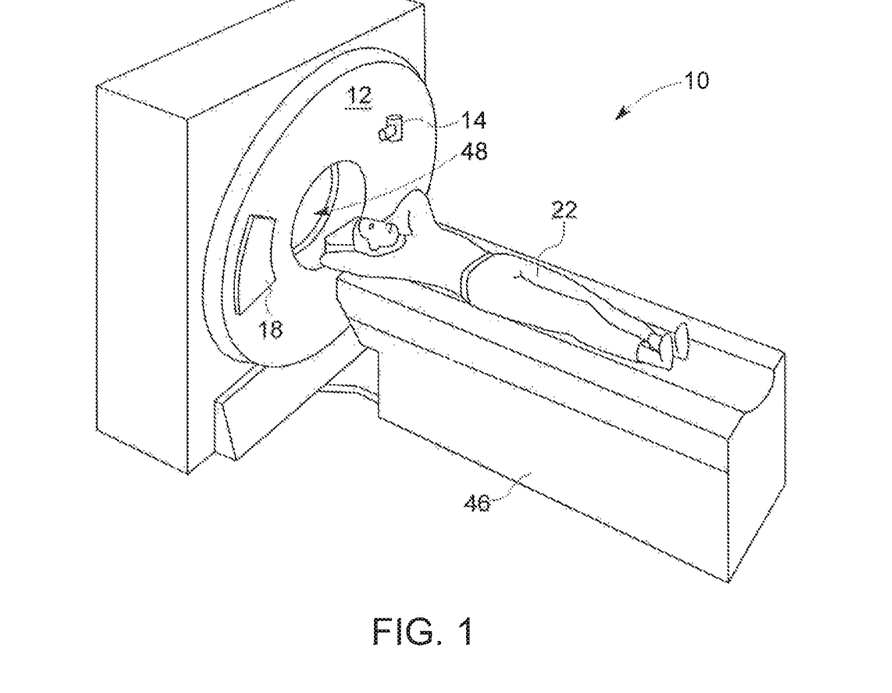
FIG. 1 is a schematic representation of a CT imaging system according to an exemplary embodiment of the invention.
Figure 2:
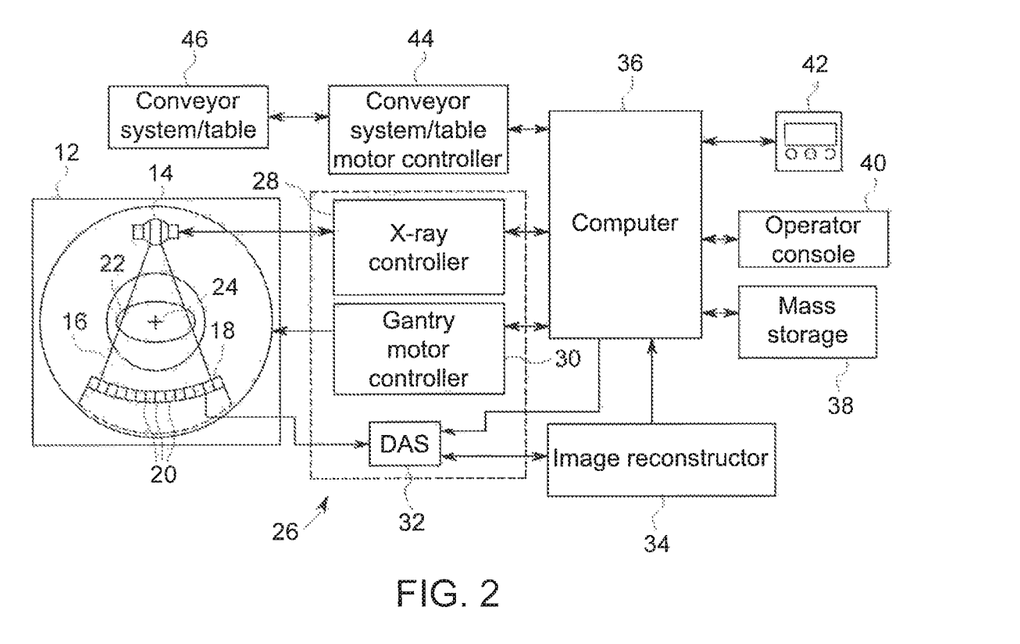
FIG. 2 is a block schematic diagram of the CT imaging system illustrated in FIG. 1.

Referring now to FIGS. 1 and 2, a CT imaging system 10 is illustrated in accordance with one exemplary embodiment of the invention that includes a gantry 12 and an X-ray source 14, which typically is an X-ray tube that projects a beam of X-rays 16 towards a detector array 18 positioned opposite the X-ray tube on the gantry 12. In one embodiment, the gantry 12 may have multiple X-ray sources within the gantry that project beams of X-rays towards at least one detector array or multiple detector arrays. The detector array 18 is formed by a plurality of detector elements 20 which together sense the projected X-rays that pass through an object to be imaged, such as a patient 22. During a scan to acquire X-ray image data, the gantry 12 and the components mounted thereon rotate about a center of rotation 24. While the CT imaging system 10 is described with reference to a patient 22 in a healthcare setting, it should be appreciated that the CT imaging system 10 may have applications outside a healthcare realm. For example, the CT imaging system 10 may be utilized for ascertaining the contents of closed articles, such as luggage, packages, etc., in search of contraband such as explosives and/or biohazardous materials, and inspection of other structures or objects.

Rotation of the gantry 12 and the operation of the X-ray source 14 are governed by a control mechanism 26 of the CT system 10. The control mechanism 26 includes an X-ray controller 28 that provides power and timing signals to the X-ray source 14 and a gantry motor controller 30 that controls the rotational speed and position of the gantry 12. A data acquisition system (DAS) 32 in the control mechanism 26 samples data from the detectors 20 and converts the data to digital signals for subsequent processing. An image reconstructor 34 receives sampled and digitized X-ray data from the DAS 32 and performs image reconstruction. The reconstructed images are applied as an input to a computer 36, which stores the images in a mass storage device 38 for further processing or viewing.

Moreover, the computer 36 also receives commands and scanning parameters from an operator via operator console 40 that may have an input device such as a keyboard (not shown in FIGS. 1-2). An associated display 42 allows the operator to observe the reconstructed images and other data from the computer 36. Commands and parameters supplied by the operator are used by the computer 36 to provide control and signal information to the DAS 32, the X-ray controller 28 and the gantry motor controller 30. In addition, the computer 36 operates a table motor controller 44, which controls a motorized table 46 to position the patient 22 and the gantry 12. Particularly, the table 46 moves portions of patient 22 through a gantry opening 48. It may be noted that in certain embodiments, the computer 36 may operate a conveyor system controller 44, which controls a conveyor system 46 to position an object, such as, baggage or luggage and the gantry 12. More particularly, the conveyor system 46 moves the object through the gantry opening 48.

Figure 3:
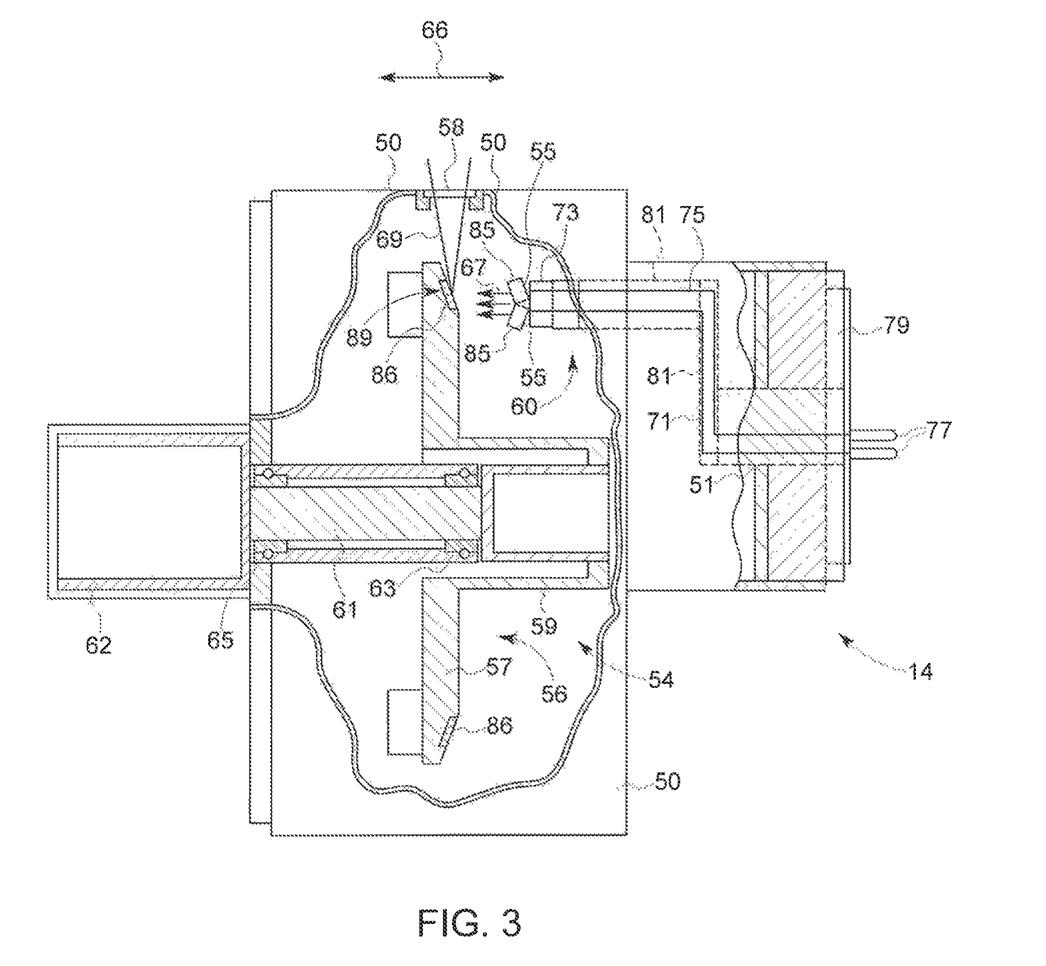
FIG. 3 is a cross-sectional view of an X-ray tube incorporating exemplary embodiments of the invention.

FIG. 3 illustrates a cross-sectional view of an X-ray tube 14 incorporating embodiments of the invention. X-ray tube 14 includes a frame 50 that encloses a vacuum region 54, with an anode assembly 56 and a cathode assembly 60 positioned therein. Anode assembly 56 includes a target 57 having a target track 86, and a target hub 59 attached thereto. Terms "anode" and "target" are to be distinguished from one another, where target typically includes a location, such as a focal spot, wherein electrons impact a refractory metal with high energy in order to generate X-rays, and the term anode typically refers to an aspect of an electrical circuit which may cause acceleration of electrons theretoward. Anode assembly 56 includes a shaft 61 supported by a front bearing 63 and a rear bearing 65. Shaft 61 is attached to a rotor 62. Cathode assembly 60 includes a emitter support structure or cathode cup assembly 73 and a pair of flat emitters or filaments 55, which can be formed to be identical to one another, as mirror images of one another, or differently from one another, disposed on the cathode cup assembly 73 at an angle with regard to one another and coupled to a current supply lead 71 and a current return 75 that each pass through a center conductor assembly 51.

Feedthrus 77 pass through an insulator 79 and are electrically connected to electrical leads 71 and 75. X-ray tube 12 includes a window 58 typically made of a low atomic number metal, such as beryllium, to allow passage of X-rays therethrough with minimum attenuation. Cathode assembly 60 includes a support arm 81 that supports emitter support structure or cathode cup assembly 73, flat emitters 55, as well as other components thereof. Support arm 81 also provides a passage for leads 71 and 75. Cathode assembly 60 may include additional electrodes 85 that are electrically insulated from cathode cup assembly 73 and electrically connected via leads (not shown) through support arm 81 and through insulator 79 in a fashion similar to that shown for feedthrus 77.

In operation, anode target 57 is spun via a motor comprised of a stator (not shown) external to rotor 62. An electric current is applied to one of the flat emitters 55 via lead 71 which passes through the emitter 55, along an electrically connecting member (not shown) disposed between and connecting the emitters 55, and returns through the other opposite emitter SS through lead 75 to heat emitters 55 and emit electrons 67 therefrom. A high-voltage electric potential is applied between the anode assembly 56 and the cathode assembly 60, and the difference therebetween accelerates the emitted electrons 67 from cathode assembly 60 to anode 56. Electrons 67 impinge target 57 at target track 86 and X-rays 69 emit therefrom at a focal spot 89 and pass through window 58. At least one electrode 85 may be used to shape, deflect, or inhibit the electron beam, as is known in the art.

Figure 4:
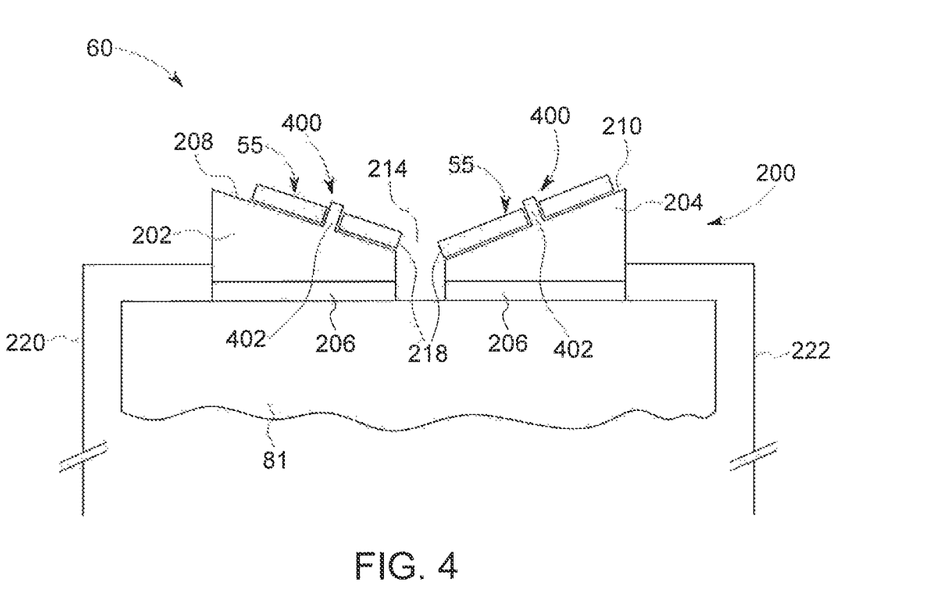
FIG. 4 is an end view of a cathode assembly according to an exemplary embodiment of the invention.

Referring now to FIG. 4, a portion of an exemplary embodiment of a cathode assembly 60 is illustrated therein. That illustrated in FIG. 4 is illustrated from a different vantage point than that illustrated in FIG. 3. Cathode assembly 60 in the illustrated exemplary embodiment includes a cathode support arm 81 and an emitter support structure or cathode cup assembly 200 that in one embodiment includes a first portion 202 and a second portion 204 that are connected to cathode support arm 81 and having an insulating material 206 positioned to insulate first and second portions 202, 204 from cathode support arm 81. The flat emitters 55 are positioned therein to define a gap 214 therebetween, and are mechanically coupled to first and second portions 202, 204 at each end of each emitter 55. According to exemplary embodiments of the invention, the flat emitters 55 can be mechanically attached to adjacent first and second attachment surfaces 208, 210 of the first and second portions 202, 204 using laser brazing or laser welding, as examples. According to one embodiment, first and second portions 202, 204 may each include a step or cutout portion (not shown) having a depth that is comparable to a thickness of the flat emitters 55. In such fashion, when electrons are caused to emit from a planar emitting surface of flat emitters 55, such as electrons 67 illustrated in FIG. 3, according to this embodiment electrons 67 are prevented from emitting from side edges of the emitters 55.

Electrical current is carried to the flat emitter 55 on first portion 202 via a current supply line 220 and from the flat emitter 55 on second portion 204 via a current return line 222 which are electrically connected to X-ray controller 28 and optionally controlled by computer 36 of system 10 in FIG. 2. Incidentally, current supply and return lines 220 and 222 correspond to current supply lead 71 and current return 75 illustrated in FIG. 3. And, although current supply and return lines 220, 222 are illustrated as external to cathode support arm 81, according to other embodiments, current supply and return lines 220, 222 may pass through cathode support arm 81 and insulating material 206.

Figure 5:
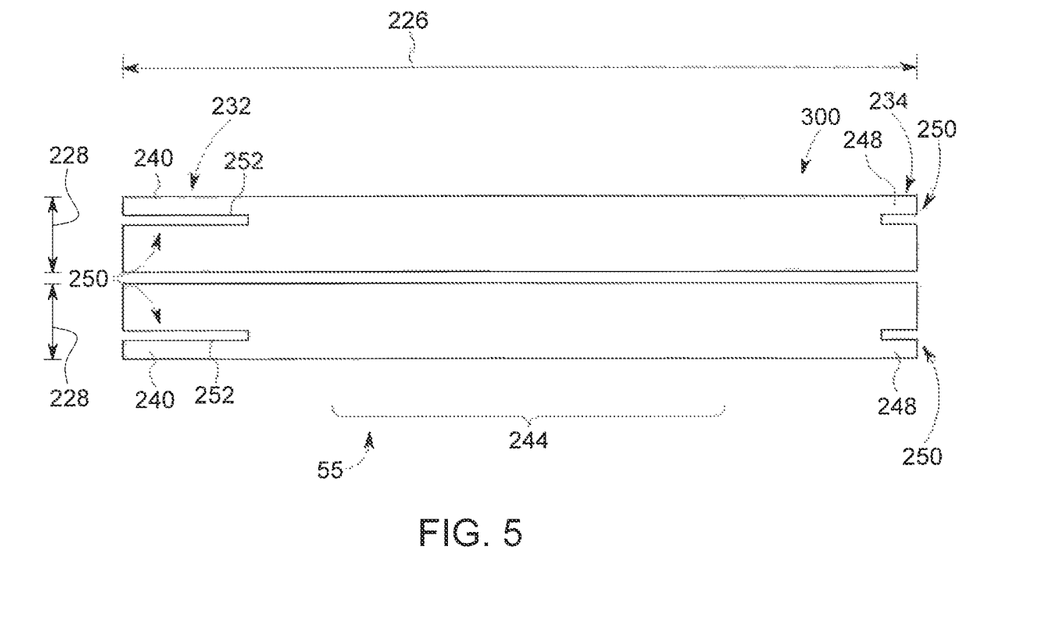
FIG. 5 is a top plan view of an emitter pair in accordance with an exemplary embodiment of the invention.

With reference to the illustrated exemplary embodiment of FIGS. 4-5, and to the entire disclosure of co-pending and co-owned U.S. patent application Ser. No. 15/614,018, entitled Flat Emitters With Stress Compensation Features, the entirety of which is expressly incorporated herein for all purposes, the flat emitters 55 include a length 226 and a width 228, as shown in FIG. 5. Length 226 corresponds to the profile view of flat emitter 55 as shown in FIG. 5, and width 228 extends normal to the profile in FIG. 5. Length 226 is greater than width 228. Further, in one exemplary embodiment the length 226 of the emitter 55 is twice as long or more as the width 228 enabling the emitter 55 to produce sufficient electron emission across the emission surface defined between the first mechanical engagement region 232 and second mechanical engagement region 234 defined on the emitter 55.

Each flat emitter 55 includes first and second mechanical engagement regions 232, 234 located at opposite ends of the emitter 55 along length 226. First and second mechanical engagement regions 232 and 234 are secured to the first and second attachment surfaces 208 and 210 of emitter support structure 200, and may be attached thereto using spot welds, laser welds, line welds, brazing, among other known methods.

Each emitter 55 is formed with a first engagement region 232 and a second engagement region 234 at opposite ends of the length 226 of the emitter 55. First engagement region 232 is formed with a first contact 240 connected to an emission region 244 that is formed with a suitable emission geometry, and a second contact 248 connected to the emission region opposite the first contact 240, with each emission regions 244 of each emitter 55 separated by the gap 214. The end of each emission region 244 adjacent the first and second contacts 240, 248 is operably engaged with the current supply line 220 and the return line 222 in a known manner to supply current to the emission regions 244 of the emitters 55. The first and second engagement regions 232, 234 of each emitter 55 are electrically isolated so that the current flows through the emission regions 244 of each emitter 55, heating the emission regions 244 to a temperature of above 2000 degrees Celsius (° C.), and in one exemplary embodiment between 2000° C. and 2700° C. or between 2200° C. and 2500° C., or more, in order to cause the emission region 244 to generate a flow of electrons therefrom.

In order to mechanically connect the emitters 55 to the first and second portions 202, 204, the emitters 55 include locating features 250 at each end of the emitter 55 within first and second mechanical engagement regions 232, 234. The locating features 250 can take any shape desired, such as any number of apertures or slots, and in the illustrated exemplary embodiment of FIG. 5, the locating features 250 are formed as elongate slots 252 the extend inwardly from the opposed ends of the emitter 55 into the respective first and second mechanical engagement regions 232, 234.

Figure 6:
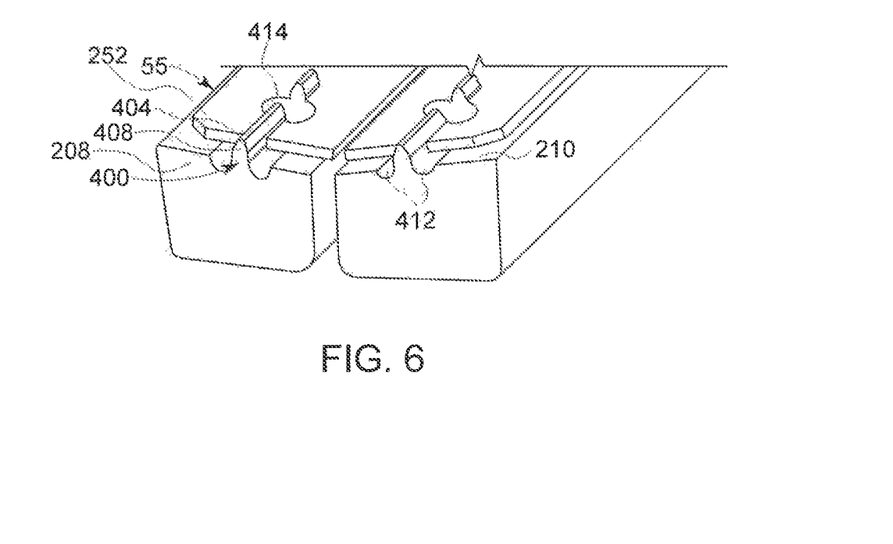
FIG. 6 is a partially broken away, isometric view of an emitter support structure and emitter pair in accordance with an exemplary embodiment of the invention.
Figure 7:
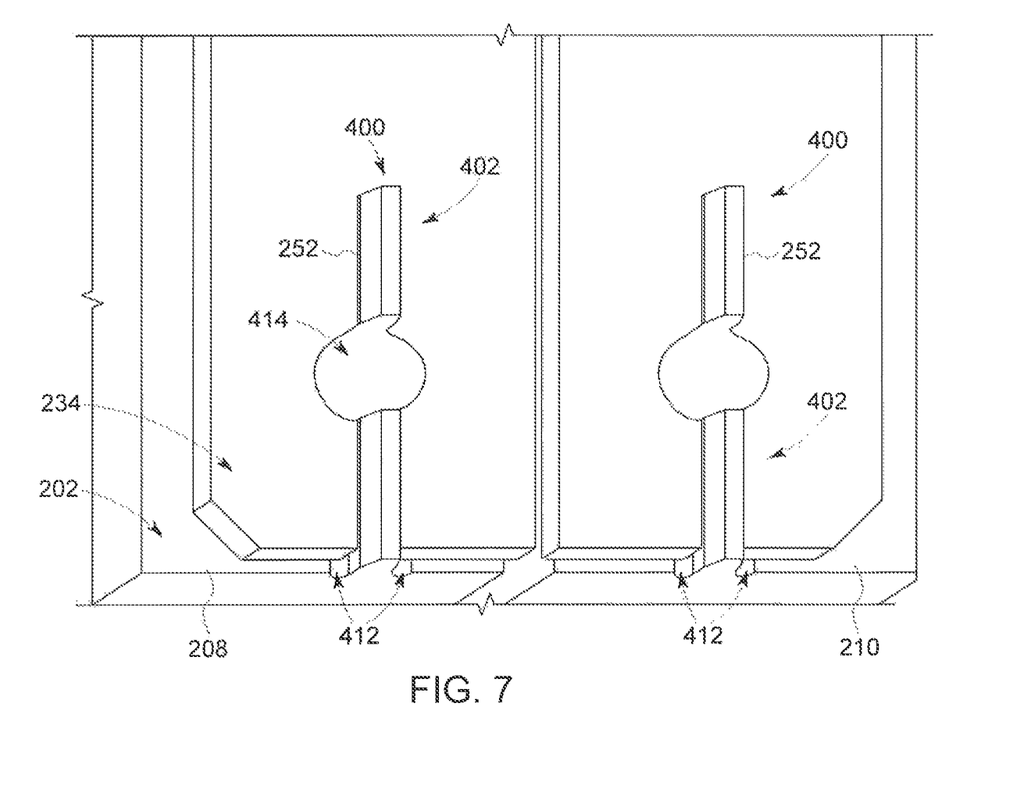
FIG. 7 is a top plan view of mounting members securing emitters to an emitter support structure of FIG. 6 in accordance with an exemplary embodiment of the invention.

Looking now at FIGS. 4, 6 and 7, each first and second portion 202, 204 includes a mounting member 400 disposed on the first and second attachment surfaces 208, 210 of each first and second portion 202, 204. Each mounting member 400 extends outwardly from the first and second attachment surfaces 208, 210, and in the illustrated exemplary embodiment of FIGS. 4, 6 and 7, and extend outwardly perpendicularly to first and second attachment surfaces 208, 210. The mounting members 400 are formed of a material suitable for forming a weld between the emitter 55 and the first and second attachment surfaces 208, 210 in order to secure the emitter 55 to the first and second attachment surfaces 208, 210. The mounting members 400 can be formed separately from the first and portions 202, 204 and affixed thereto, such as platinum mounting members, or as shown in the exemplary illustrated embodiment of FIGS. 4, 6 and 7, and can be formed integrally with the first and second portions 202, 204, which are formed of suitable materials, such as Kovar, among other weldable or braxable metal materials. In the illustrated exemplary embodiment, the mounting member 400 is formed as a raised ridge 402 that extends along at least a portion of the length of the first and second portion 202, 204. The raised ridges 402 extend above the emitters 55 and are heated and melted by laser welding or brazing or other suitable technique, so that the material forming the raised ridge 402 forms a weld 414 securing the emitters 55 to the first and second portions 202, 204. For example, the raised ridges 402 are welded to the emitters 55 so that it forms a mushroom-shaped weld bead over the emitters 55, see FIG. 7. The welding heats and melts the raised ridges 402 over the emitters 55 joining the emitters 55 to the emitter support structure or cathode cup assembly 200. The emitters 55 are welded or brazed directly to the support structure or cathode cup assembly 200 without a filler material. The process of a direct weld or braze eliminates the need for a filler material that is used in most other welding or brazing processes.

To enable the emitters 55 to be securely engaged with the first and second portions 202, 204, the geometry of the mounting members 400 corresponds to that of the locating features 250 on the emitters 55, such that when the emitters 55 are positioned on the first and second portions 202, 204, the tolerance between the locating features 250 and the mounting members 400 limits and/or prevents movement of the emitters 55 with regard to the first and second portions 202, 204 in other than the vertical direction, i.e., the direction in which the mounting members 400 extend form the first and second portions 202, 204. In the exemplary embodiment of FIGS. 6 and 7, the locating feature 250 is formed as an elongate slot 252 having a width complementary to the width of the mounting member 400, which takes the form of the raised ridge 402. In particular, the width of the slot 252 is formed to closely approximate the width of a lower section 408 of the raised ridge 402, enabling the raised ridge 402, and in particular the lower section 408 to easily and securely position the emitter 55 as desired on the first and second portions 202, 204. An upper section 404 of the raised ridge 402 is located above the lower section 408 of the raised ridge 402 and facilitates the placement of the slot 252 around the raised ridge 402 due to the smaller width of the upper section 404 compared to lower section 408.

Looking again at the illustrated exemplary embodiment of FIGS. 6 and 7, the first and second attachment surfaces can optionally include recesses 412 disposed on one or both sides of each mounting member 400. The recesses 412 function to thermally insulate the emitter 55 from the mounting member 400 and to minimize any thermal stresses generated within the emitter 55 due to the heating of the mounting members 400. The recesses 412 can be formed as desired and in the illustrated exemplary embodiment are formed as curved recesses 412 that extend along the length of each side of the raised ridge 402.

In an exemplary method of securing an emitter 55 to the first and second portions 202, 204 of the support structure or cathode cup assembly 200, initially the emitters 55 are positioned on the first and second attachment surfaces 208, 210 of the first and second portions 202, 204 such that the mounting members 400 are positioned within the locating features 250 located on the emitters 55. Once the emitters 55 are positioned in a co-planar position flush against the first and second attachment surfaces 208, 210 to facilitate the electrical connection of the emitters 55 to the leads 220, 222, the mounting member 400 is directly heated in order to melt the material of the mounting member 400. The heating of the mounting member 400 can be accomplished in any suitable manner to sufficiently heat the mounting member 400 to melt it, such as by laser welding the mounting member 400. In melting the mounting members 400, and in particular the upper section 404 of the mounting member 400, the material forming the upper section 404 flows over the edges of the locating feature 250 to from a mushroom-shaped weld bead 414 over a portion of the first and second mechanical engagement regions 232, 234 of the emitter 55, as shown in FIG. 7. When cooled, the bead 414 is integrally connected to the lower section 408 of the mounting member 400 and positioned directly on and over the emitter 55 to constrain movement of the emitter 55 vertically with regard to the mounting member 400, e.g., the direction of the height of the raised ridge 402 extending away from the first and second attachment surfaces 208, 210.

In alternative embodiment of the disclosure, the cup portions 202, 204 can be formed to receive one or more emitters 55 and to position the emitters 55 at angles with respect to the remainder of the cathode assembly 60 and optionally to one another. Further, the mounting structures 400 can be formed to have any desired number or shape on to correspond to the shape and number of the locating features 250 present on the emitters 55, such as elongate ridges, posts, or other suitable structures, that are machined directly on or formed separately from and secured to the first and second portions 202, 204 and/or first and second attachment surfaces 208, 210. Further, to secure the emitters 55 to the first and second portions 202, 204, the mounting members 400 can be melted at a number of points along its length, thereby providing multiple points of attachment between the emitters 55 and the first and second portions 202, 204 while using only a single mounting member 400.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An emitter support structure adapted for use with an X-ray tube, the emitter support structure comprising:
   a first portion and a second portion that are connected to a cathode support arm; and
   a mounting member disposed on a first attachment surface of the first portion and a mounting member disposed on a second attachment surface of the second portion, wherein each of the mounting members extends outwardly from the first and second attachment surfaces and each includes a deformed portion and at least one non-deformed portion adjacent the deformed portion, and wherein the deformed portion is formed after positioning an emitter on the mounting member.

2. The emitter support structure of claim 1, wherein each of the mounting members is integrally formed with the first and second attachment surfaces.

3. The emitter support structure of claim 2, wherein each of the mounting members is formed as a raised ridge that extends along at least a portion of the length of the first and second portions.

4. The emitter support structure of claim 3, wherein each of the raised ridges comprise:
   a lower section disposed on each of the first and second attachment surfaces; and
   an upper section located above the lower section to facilitate attachment of an emitter on the emitter support structure.

5. The emitter support structure of claim 4, wherein the lower section and the upper section have different widths.

6. The emitter support structure of claim 1, further comprising at least one recess disposed on each of the first and second attachment surfaces adjacent each of the mounting members.

7. The emitter support structure of claim 1, wherein each of the mounting members extends perpendicular from the first and second attachment surfaces.

8. An X-ray tube comprising:
   a cathode assembly; and
   an anode assembly spaced from the cathode assembly, wherein the cathode assembly comprises:
   an emitter support structure comprising:
   a first portion and a second portion that are connected to a cathode support arm;
   a first mounting member disposed on a first attachment surface of the first portion; and
   a second mounting member disposed on a second attachment surface of the second portion, wherein the first mounting member and the second mounting member each extends outwardly from the first attachment surface and the second attachment surface and each includes a deformed portion and at least one non-deformed portion adjacent the deformed portion; and
   at least one emitter disposed on the emitter support structure, the at least one emitter including at least one locating feature disposed around and at least partially overlapped by the deformed portion of at least one of the first mounting member or the second mounting member,
   wherein the deformed portion is formed after positioning the at least one emitter on the first or second mounting member.

9. The X-ray tube of claim 8, wherein the at least one locating feature is an elongate slot.

10. The X-ray tube of claim 8, wherein the at least one locating feature is at least one elongate slot disposed at each end of the at least one emitter.

11. The X-ray tube of claim 8, wherein the at least one locating feature is formed complementary to the at least one mounting member.

12. The X-ray tube of claim 8, wherein the at least one mounting member comprises:
   a first section extending from the emitter support structure and extending into the at least one locating feature; and
   a second section extending from the first section and extending above the at least one locating feature.

13. The X-ray tube of claim 12, wherein the first and second sections are integrally formed with the emitter support structure.

14. A method for forming a cathode assembly used in an X-ray tube, the method comprising the steps of:
- providing an emitter support structure including an emitter attachment surface having at least one mounting member thereon;
- providing at least one emitter including at least one locating feature thereon;
- positioning the at least one emitter on the emitter support structure with the at least one locating feature disposed at least partially around the at least one mounting member; and
- heating the at least one mounting member to deform the at least one mounting member to overlap a portion of the at least one emitter and secure the at least one emitter to the emitter attachment surface prior to passing current through the at least one emitter.

15. The method of claim 14, wherein the at least one mounting member includes a first section positioned on the emitter attachment surface and a second section disposed on the first section, and wherein the step of heating the at least one mounting member comprises heating the second section.

16. The method of claim 15, wherein the first and second sections are integrally formed with the emitter attachment surface.

17. The method of claim 15, wherein the step of heating the second section comprises melting the second section to enable the second section to flow over the at least one emitter to secure the at least one emitter to the emitter attachment surface.

18. The method of claim 14, wherein the at least one locating feature is formed complementary to the at least one mounting member, and wherein the step of positioning the at least one emitter on the emitter attachment structure comprises engaging the at least one mounting member with the at least one locating feature.

\* \* \* \* \*